United States Patent [19]
Kessler et al.

[11] Patent Number: 5,610,753
[45] Date of Patent: Mar. 11, 1997

[54] OPTICAL DESIGN OF LASER SCANNER TO REDUCE THERMAL SENSITIVITY

[75] Inventors: David Kessler, Rochester; Michael E. Harrigan, Webster, both of N.Y.

[73] Assignee: Eastman Kodak Company, Rochester, N.Y.

[21] Appl. No.: 669,760

[22] Filed: Jun. 26, 1996

Related U.S. Application Data

[63] Continuation-in-part of Ser. No. 120,716, Sep. 13, 1993, abandoned, which is a continuation-in-part of Ser. No. 806,953, Dec. 12, 1991, abandoned.

[51] Int. Cl.$^6$ .................................................. G02B 26/08
[52] U.S. Cl. .......................... 359/205; 359/207; 359/820
[58] Field of Search .................................. 359/196–226, 359/820, 434, 362, 363, 399, 421; 346/107.1; 347/256–258; 372/24–25; 358/296, 474

[56] References Cited

U.S. PATENT DOCUMENTS

| | | | |
|---|---|---|---|
| 4,621,890 | 11/1986 | Suzuki et al. ........................... | 359/744 |
| 4,818,049 | 4/1989 | Assenheim et al. ..................... | 359/900 |
| 4,915,484 | 4/1990 | Yamamoto ............................... | 359/217 |
| 4,917,483 | 4/1990 | Nakao ..................................... | 359/662 |
| 4,948,221 | 8/1990 | Yates ....................................... | 385/53 |
| 4,998,790 | 3/1991 | Iizuka et al. ............................ | 359/207 |

FOREIGN PATENT DOCUMENTS

0323850  7/1989  European Pat. Off. .

*Primary Examiner*—James Phan
*Attorney, Agent, or Firm*—William F. Noval

[57] ABSTRACT

An imaging system including a Gaussian light source, such as a laser diode, an image plane, and an optical system located between the light source and the image plane. The optical system has an optical axis, a first principal focus and a second principal focus. The image plane is located at the second principal focus of the optical system. The optical system creates a Gaussian intensity profile on the image plane whose $e^{-2}$ intensity diameter on such plane is substantially constant even when the Gaussian light source being imaged by the optical system shifts along the optical axis.

8 Claims, 6 Drawing Sheets

OPTICAL DESIGN OF LASER SCANNER TO REDUCE THERMAL SENSITIVITY

CROSS-REFERENCE TO RELATED APPLICATIONS

This is a continuation-in-part application of earlier filed application Ser. No. 08/120,716, filed on 13 Sep. 1993, now abandoned, which is a continuation-in-part of earlier filed application Ser. No. 806,953, filed on Dec. 12, 1991, now abandoned.

TECHNICAL FIELD

The present invention relates in general to laser printers. In particular it relates to an optical design for a laser printer using small area highly divergent light sources such as solid state laser diodes. The optical system is designed so that the $e^{-2}$ diameter of the image forming spot or pixel is insensitive to movement of the light source with respect to the optical system. The light source motion with which the invention is concerned is along the optical axis and would most commonly be caused by thermal expansion or contraction as the temperature of the environment changes.

BACKGROUND OF THE INVENTION

The use of solid state lasers (laser diodes) in digital printers or scanners has many advantages including compact size, high power, and low cost. These light sources have a disadvantage because they require a relatively high magnification optical system making such systems sensitive to changes in the axial position of the light source. The reason for the high magnification is explained as follows.

Typically, the light emitting region of the laser diode is focused onto a light sensitive medium by an optical system. Through a variety of means, the focused spot can be scanned across the light receiving medium and turned off and on at a high rate. The light sensitive medium is exposed and the image is built up of many small spots or pixels. In a digital printer it is important to maintain a constant writing spot size, because image artifacts can appear if it is digitized with a varying size pixel. In this and the remaining description, we will define the writing spot or pixel diameter to be that diameter at which the intensity of the light is $e^{-2}$, approximately 0.1353, of the peak intensity.

The high magnification referred to above results from the fact that the light emitting region of a laser diode is very small compared to the writing spots commonly used. A typical pixel size used is that for a 300 spot per inch printer which has an $e^{-2}$ diameter of approximately 0.08 mm. The light emitting area of laser diodes ranges approximately from 0.5 to 2 microns $e^{-2}$ diameter in its smallest dimension and 2 to 6 microns in its largest dimension. The light emitting area is the contour of the light intensity at which the intensity is $e^{-2}$ of the peak intensity. Required is an optical system between the laser diode and image receiving medium having a magnification from 10 to 160 times. For example, a 1 micron laser diameter emitting area would need a magnification of 80 to make an 80 micron $e^{-2}$ diameter pixel.

A high magnification optical system has the characteristic that its image location along the optical axis is sensitive to the object position change. The longitudinal magnification which is the magnification of an infinitesimally short line along the optical axis is the square of the transversal magnification. For a system which has 80 times magnification as above, the longitudinal magnification would be 6400. This means that if the object shifts along the optical axis by 0.001 mm or 1 micron, the image will shift by 0.001 times 6400 which is 6.4 mm. A laser shift of this amount would likely cause the writing spot of a laser printer to be out of focus and increase in diameter by an unacceptably large amount. Therefore the space between the laser and the optical system must be tightly controlled. On the other hand, laser printers often need to operate in an environment whose temperature changes over a wide range. These uncontrolled temperature changes will cause the material holding the laser with respect to the optical system to expand and contract. Thermal expansion changes leading to 0.001 mm changes can very easily occur.

Normally laser printers are designed so that the Gaussian laser spot or waist is located on the image receiving medium. A "waist" is defined as the position where the minimum focused spot occurs. In general this waist position is different than the location of the geometrical optics determined conjugate point, but it can be calculated by well known procedures. The optical system of a laser printer takes the input laser waist on the object side of the optical system and creates the waist of the desired size on the output or image side of the optical system. The ratio of the image side waist to the object side waist is the transverse magnification.

One approach to stabilizing the laser diode axial position with respect to the optical system is to mount the laser and first lens of the optical system, usually a "collimator", in a thermally stable mount or "athermal head". The athermal head is carefully designed with different materials to achieve compensation so that the axial position of the lens with respect to the collimator is very stable. This approach becomes very difficult and expensive if the desired axial space control is in the range of a few tenths of microns. Also, it may not be desired to actually control the physical space between the laser and collimator lens itself because if the lens changes it paraxial characteristics with temperature, its first principal plane may shift with respect to its actual external lens surfaces. The requirement then is to stabilize the distance from the laser input waist to the first principal plane of the collimator. This means that the lens paraxial properties would have to be completely characterized thermally in order to predict the motion of the first principal plane when the temperature changes. An example of this athermal head approach is disclosed in U.S. Pat. No. 4,948,221 issued Aug. 14, 1990 to inventor Yates. This invention, however, does not take into account the optical changes of the lens with temperature.

Another approach is to actively compensate for thermal changes by sensing the image waist motion and adjusting a lens position to place the waist back to the correct position. This requires a method to detect the waist position at the image, a way to relay this information, a method to move a lens and accept the waist error signal, and a moveable lens. This results in added complexity and cost, but it has the advantage of compensating for athermal expansion and contraction throughout the optical system and not just those parts near the laser. An example of the technique is published in European Patent Application 0323850.

SUMMARY OF THE INVENTION

According to the present invention, there is provided a laser diode optical system in which the spot size, as measured by its $e^{-2}$ intensity diameter, is kept constant despite axial shifts of the laser diode with respect to the optical system. The laser diode optical system has a primary characteristic in which the image receiving medium is located at the second principal focus of the optical system between the laser diode and the image receiving medium.

The invention is based on the proof that the $e^{-2}$ diameter of the light spot measured in a plane located at the second principal focus of an optical system does not depend on the location along the optical axis of the object side or input Gaussian waist. The second principal focus, or image side principal focus is one of the six cardinal points of any optical system and is to be carefully distinguished from another focal plane. A focal plane in general depends on the location of the object and can shift over wide ranges. The focal plane of an object at infinity does coincide with the second principal focus, but in this invention, the light source is very close, has a significant numerical aperture and so is in no sense an infinite object. This is in contrast to a gas laser such as a helium-neon laser which approximates very well an object at infinity.

The fact that a Gaussian beam has a constant $e^{-2}$ diameter in this plane located at the second principal focus is not obvious. It is the object of this invention to place the image receiving medium on a plane located at the second principal focus of the optical system. It understood that the "optical system" refers to all the optical components between the laser diode and the image. When the second principal focus is thus located, then even if the waist is not on the image receiving medium, the $e^{-2}$ diameter of the Gaussian beam on the image receiving medium will not change size when the source waist shifts along the optical axis. To design a system with the image receiving medium at the second principal focus of the complete optical system requires the designer to take special care.

This invention thereby solves one of the major problems in the use of laser diode sources in laser printers and that is their sensitivity to writing spot size changes caused by small axial motions of the laser diode. This sensitivity comes from the high magnification required by laser diodes and the axial motions are most commonly caused by thermal expansion and contraction of the laser to first lens mount.

DESCRIPTION OF THE PREFERRED EMBODIMENTS

Before describing a laser diode imaging system which has the desired characteristics according to the present invention, the constancy of the $e^{-2}$ diameter of the Gaussian spot at the second principal focus will be mathematically proved.

Figure 1:
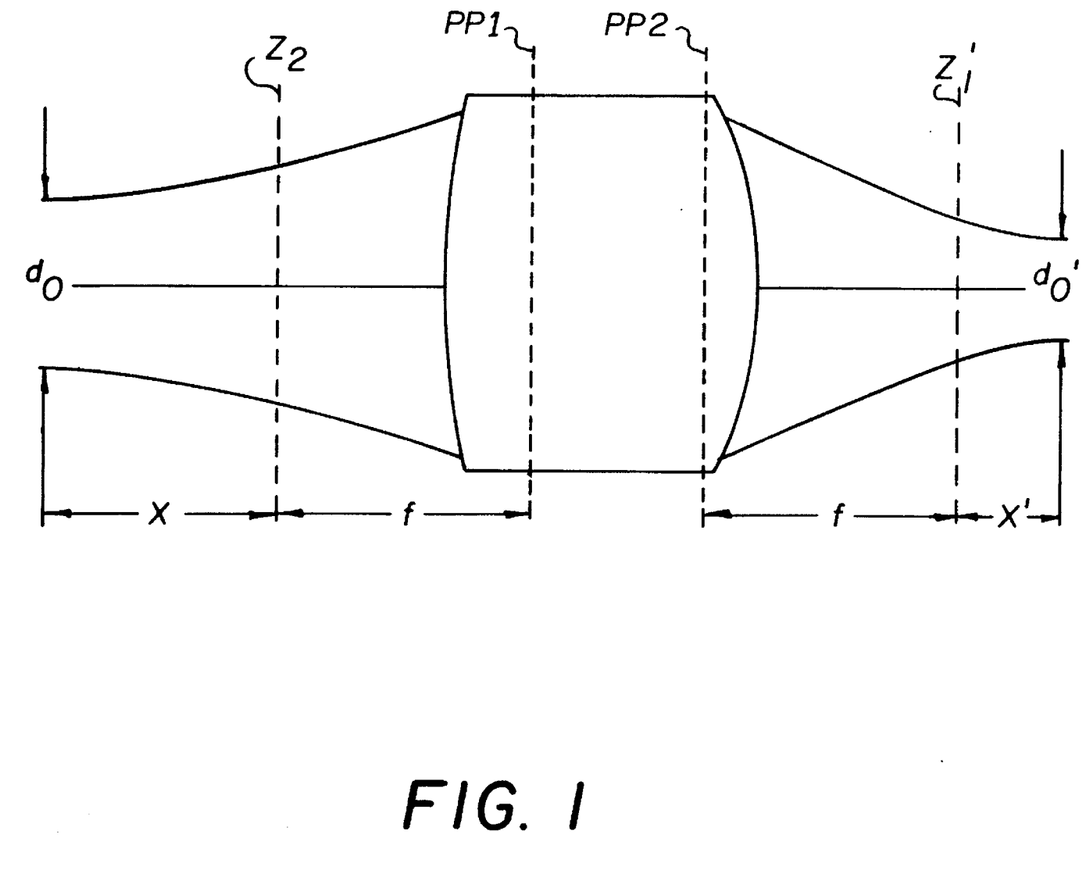
FIG. 1 is a block diagram of an arbitrary optical system imaging a Gaussian waist.

FIG. 1 shows a block diagram which includes an optical system diagrammatically shown with its principal planes PP1, PP2, its focal length f and its two principal focal foci each located a distance f from its corresponding principal plane. While only a single lens is shown for simplicity, it is to be understood that this includes the possibility of a complex multiple lens component system. Any complex multiple lens component system can be characterized by its six cardinal points: the two principal planes, two nodal points, and two principal foci.

It is also to be understood that in general, the object space medium or image medium may be different. To simplify the proof, it is assumed that both the object and image are in the same medium, but the proof can be easily extended for the more general case as well.

Also, it is to be understood that the proof applies to the more general possibility of an anamorphic optical system which lacks rotational symmetry about the optical axis. In the simplest case of an orthogonal anamorphic system, each principal section of the optical system would have its own focal length, principal planes, and principal focal points. Because of orthogonality, the proof can be applied to each section of the anamorphic optical system independently.

FIG. 1 shows a Gaussian beam waist of $e^{-2}$ diameter $d_0$ located a distance x from the first principal focus on the object side of the optical system. The optical system forms a Gaussian waist of $e^{-2}$ diameter $d'_0$ at a distance x' from the second principal focus on the image side of the optical system.

The notation follows that given in "Elements of Modern Optical Design" by Donald C. O'Shea, pages 235–237.

The object of the proof is to show that the $e^{-2}$ diameter of the light intensity in the plane located at the second principal focus does not depend on the location, x, of the object waist $d_0$.

Let the $e^{-2}$ diameter of the light intensity in the plane located at the second principal focus be d. If the wavelength, $\lambda$, of the light is known and the waist $d'_0$ is known, then one can compute the $e^{-2}$ diameter at an arbitrary position, x', from the waist from:

$$d = d'_0 \sqrt{1 + \left(\frac{4\lambda x'}{\pi d_0'^2}\right)^2} \qquad 1)$$

The distance x' is given as:

$$x' = \alpha^2 x$$

In this equation, $\alpha$ is the transverse magnification between the waists:

$$d'_0 = \alpha d_0$$

It is easily seen that:

$$\frac{x'}{d_0'^2} = \frac{\alpha^2 x}{\alpha^2 d_0^2} = \frac{x}{d_0^2}$$

Putting this result and substituting for $d'_0$ in Equation 1, it is found that:

$$d = \alpha d_0 \sqrt{1 + \left(\frac{4\lambda x}{\pi d_0^2}\right)^2} \qquad 2)$$

The magnification, α, is determined by the focal length of the optical system, f, the distance x, and $d_0$ as:

$$\alpha = \frac{f}{\sqrt{x^2 + \left(\frac{\pi d_0^2}{4\lambda}\right)^2}} = \frac{f}{\frac{\pi d_0^2}{4\lambda}\sqrt{1 + \left(\frac{4\lambda x}{\pi d_0^2}\right)^2}}$$

If this is substituted into Equation 2 above for d, then after canceling the radical terms:

$$d = \frac{d_0 f}{\frac{\pi d_0^2}{4\lambda}} = \frac{4\lambda f}{\pi d_0}$$

Since this equation does not contain any explicit or implicit dependence on x, the result has been proved. The $e^{-2}$ diameter of the light intensity on a plane at the second principal focus depends only on the wavelength, focal length, and input waist diameter.

Figure 2:
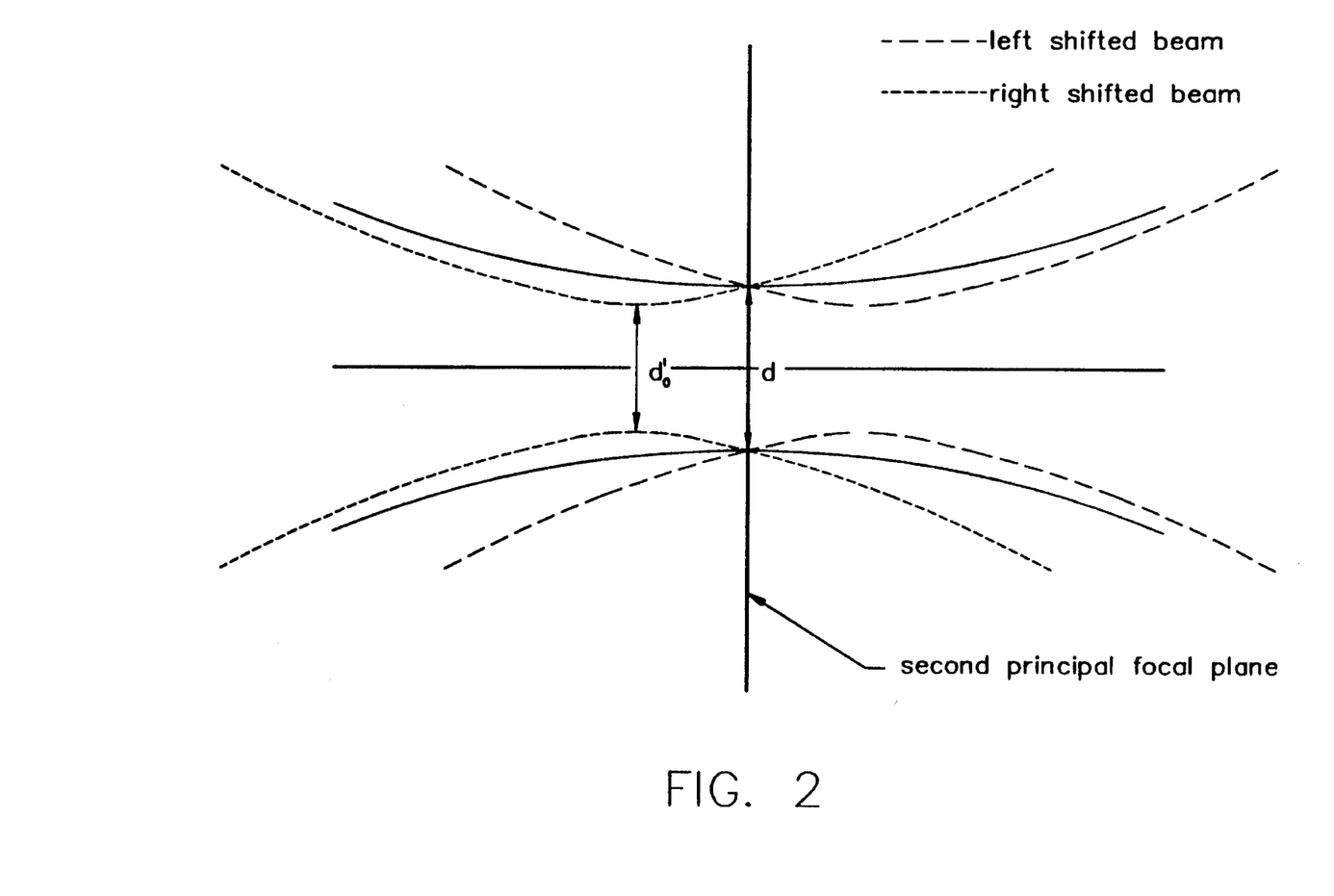
FIG. 2 is a diagram showing shifting Gaussian waists at an image surface and the $e^{-2}$ beam diameter at the image.

It is important to note that the waist, or minimum $e^{-2}$ diameter, does change size and shift when the input laser waist shifts along the optical axis. FIG. 2 is a drawing showing what actually occurs when the input laser waist shifts. The solid curved lines have a minimum separation d on the plane labeled the second principal focal plane. This is the waist position when the input waist is at its nominal position. As the input laser waist shifts away from the optical system, the output waist shifts towards the optical system as shown by the short dashed curves and the waist diameter $d'_0$. When the input laser waist moves towards the lens by some amount, the output waist gets smaller and shifts away from the lens as shown by the long dashed curves. But as can be seen in both cases, the $e^{-2}$ diameter d remains the same at the plane located at the second principal focus.

The preferred embodiment of the invention has the second principal focus of the optical system located on the image receiving medium and the laser source located at the first principal focus of the optical system. In this case the image side waist is also located on the image receiving medium. This arrangement allows a less complex optical design because of the smaller numerical aperture needed. The situation is a fixed source size and divergence and a desired image pixel or $e^{-2}$ diameter. In this case, the numerical aperture of the optical system is the smallest. The reason for this is that if the $e^{-2}$ diameter on the image receiving medium is achieved with the waist shifted some distance away, then that waist will need to be smaller than the desired $e^{-2}$ diameter. Otherwise, the $e^{-2}$ diameter on the image will be too large. A smaller waist requires a larger convergence angle of the light into the waist by the following relation:

$$d = \frac{4\lambda}{\pi\theta}$$

In this equation, d is the waist diameter (smallest $e^{-2}$ diameter), λ the wavelength of the light, and θ is the total convergence angle of the light forming the waist as measured to the $e^{-2}$ intensity lines.

Consequently, having the waist located on the second principal focus results in the smallest numerical aperture requirement thus making the optical aberration correction easier.

A second embodiment is to have the source located away from the first principal focus, but it maintains the image receiving medium at the second principal focus. This embodiment may require more complex optics to achieve the smaller waist as explained above.

Figure 3:
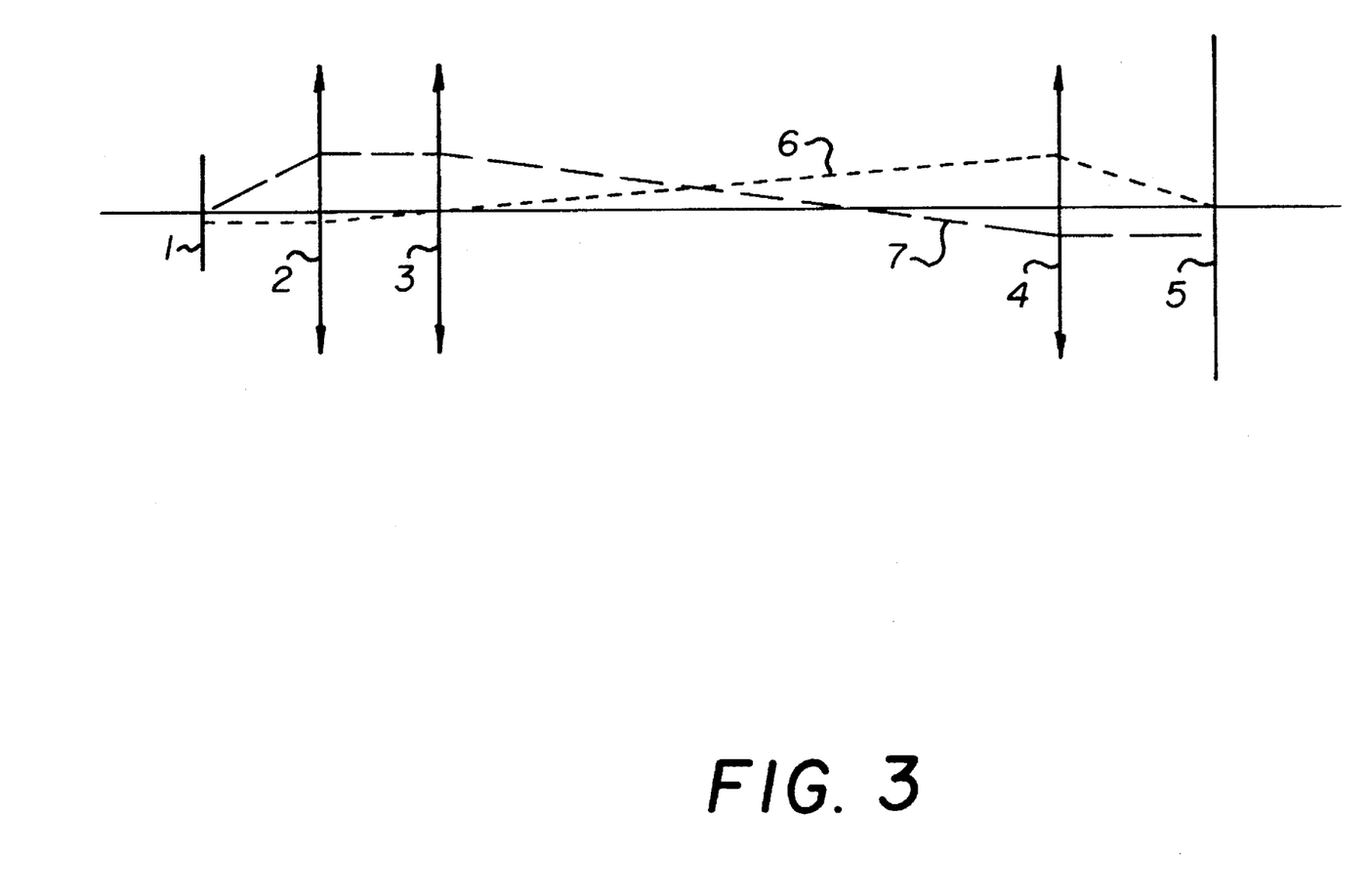
FIG. 3 is a diagram of three ideal thin lenses showing an example of the preferred embodiment with the image receiving medium at the second principal focus and the laser at the first principal focus.
Figure 4:
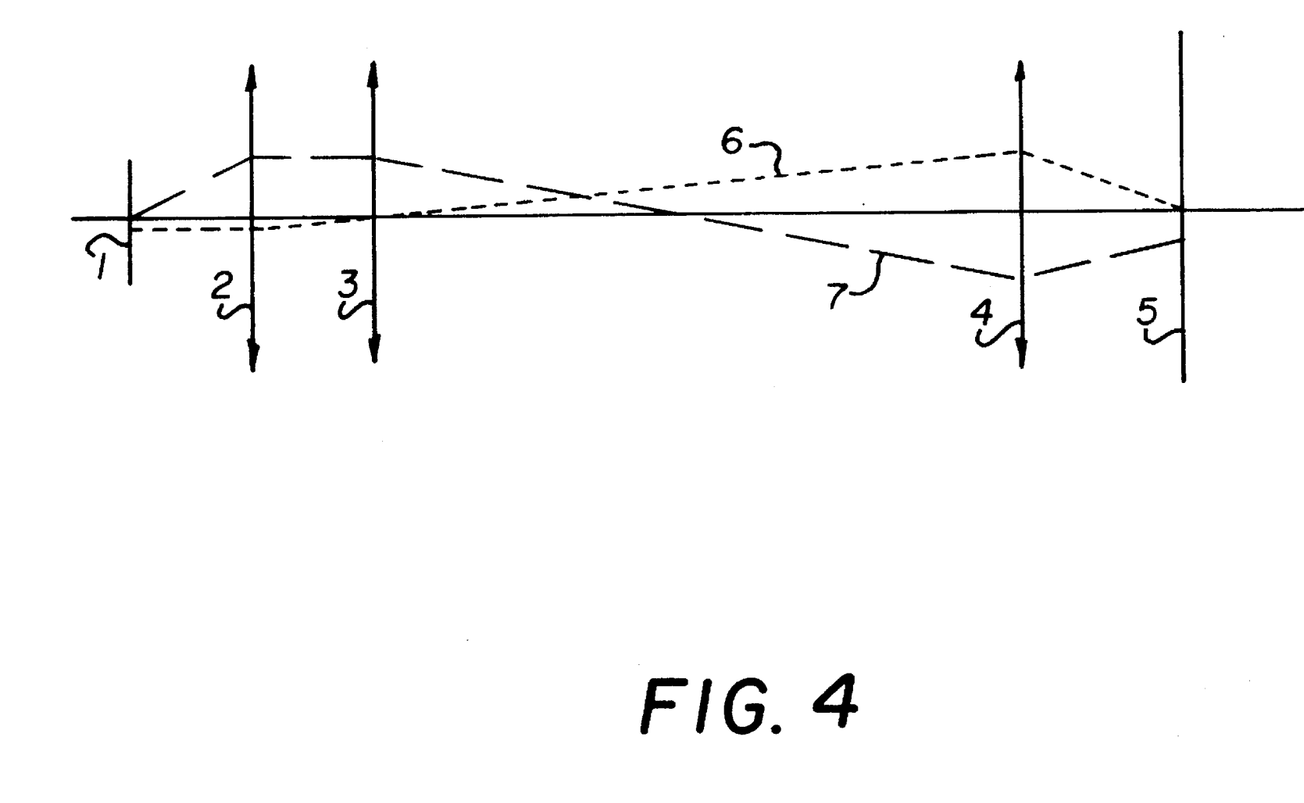
FIG. 4 is a diagram of three ideal thin lenses showing a second embodiment with the image at the second principal focus, but the laser is not at the first principal focus.

Examples of these two embodiments are shown in FIG. 3 and FIG. 4. These figures show simple ideal thin lens solutions with actual data which can be verified. The design data is as follows:

Object Gaussian beam diameter=0.004 mm

Image Gaussian beam $e^{-2}$ diameter=0.16 mm

Wavelength of light=0.0005 mm

FIG. 3 shows an example of the preferred embodiment. The object beam, 1, is imaged by three positive lenses 2, 3, and 4, onto the image receiving medium 5. The focal length of lens 2 is 4 mm, lens 3 is 16.001 mm, and lens 4 is 4.035 mm. Lens 2 is located 4 mm to the right of laser 1. Lens 3 is located 4 mm to the right of lens 2. Lens 4 is located 20.057 mm to the right of lens 3, and the image receiving medium is located 5.0514 mm to the right of lens 4. The figure also shows two paraxial rays. Ray 6 is a ray entering lens 2 parallel to the optical axis. It converges to the axial image point on 5 as it should since 5 is located at the second principal focus. Paraxial ray 7 is a ray which starts with zero height from the object laser and it exits parallel to the optical axis on the image side as it should since the object laser is located at the first principal focus of the optical system in this embodiment.

When the object laser, 1, is shifted 0.2 mm farther from lens 2, the image waist shifts from the image medium toward lens 4 by 4.996 mm, the waist reduces in diameter to 0.020 mm, but the $e^{-2}$ diameter remains the same at 0.16 mm on the image medium. Likewise, if the laser shifts by 0.2 mm closer to lens 2, the image waist moves away from the image medium by 4.996 from lens 4, with the image waist reducing to 0.02 mm diameter, but the $e^{-2}$ diameter remains the same at 0.16 mm on the image medium.

FIG. 4 shows a second embodiment in which the object laser is no longer at the first principal focus of the optical system. The object beam, 1, is imaged by three positive lenses 2, 3, and 4, onto the image receiving medium 5. The focal length of lens 2 is 4 mm, lens 3 is 14.103 mm, and lens 4 is 4.250 mm. Lens 2 is located 4 mm to the right of laser 1. Lens 3 is located 4 mm to the right of lens 2. Lens 4 is located 21.347 mm to the right of lens 3, and the image receiving medium 5 is located 5.3037 mm to the right of lens 4. The figure also shows two paraxial rays. Ray 6 is a ray entering lens 2 parallel to the optical axis. It converges to the axial image point on 5 as it should since 5 is located at the second principal focus. Paraxial ray 7 is a ray which starts with zero height from the object laser but it does not exit parallel to the optical axis on the image side since the object laser is not located at the first principal focus of the optical system.

In this design, the image waist is located 4.9306 mm towards lens 4 and is 0.02 mm in diameter while the $e^{-2}$ diameter at the image plane is 0.16 mm. When the object laser, 1, is shifted 1 mm farther from lens 2, the image waist shifts from the image medium toward lens 4 by 6.159 mm, the waist reduces from 0.02 mm in diameter to 0.0033 mm, but the $e^{-2}$ diameter remains the same at 0.16 mm on the image medium. Likewise, if the laser shifts by 1 mm closer to lens 2, the image waist moves away from the image medium by 4.103 from lens 4, with the image waist reducing from 0.02 mm diameter to 0.00494 mm, but the $e^{-2}$ diameter remains the same at 0.16 mm on the image medium.

Figure 5:
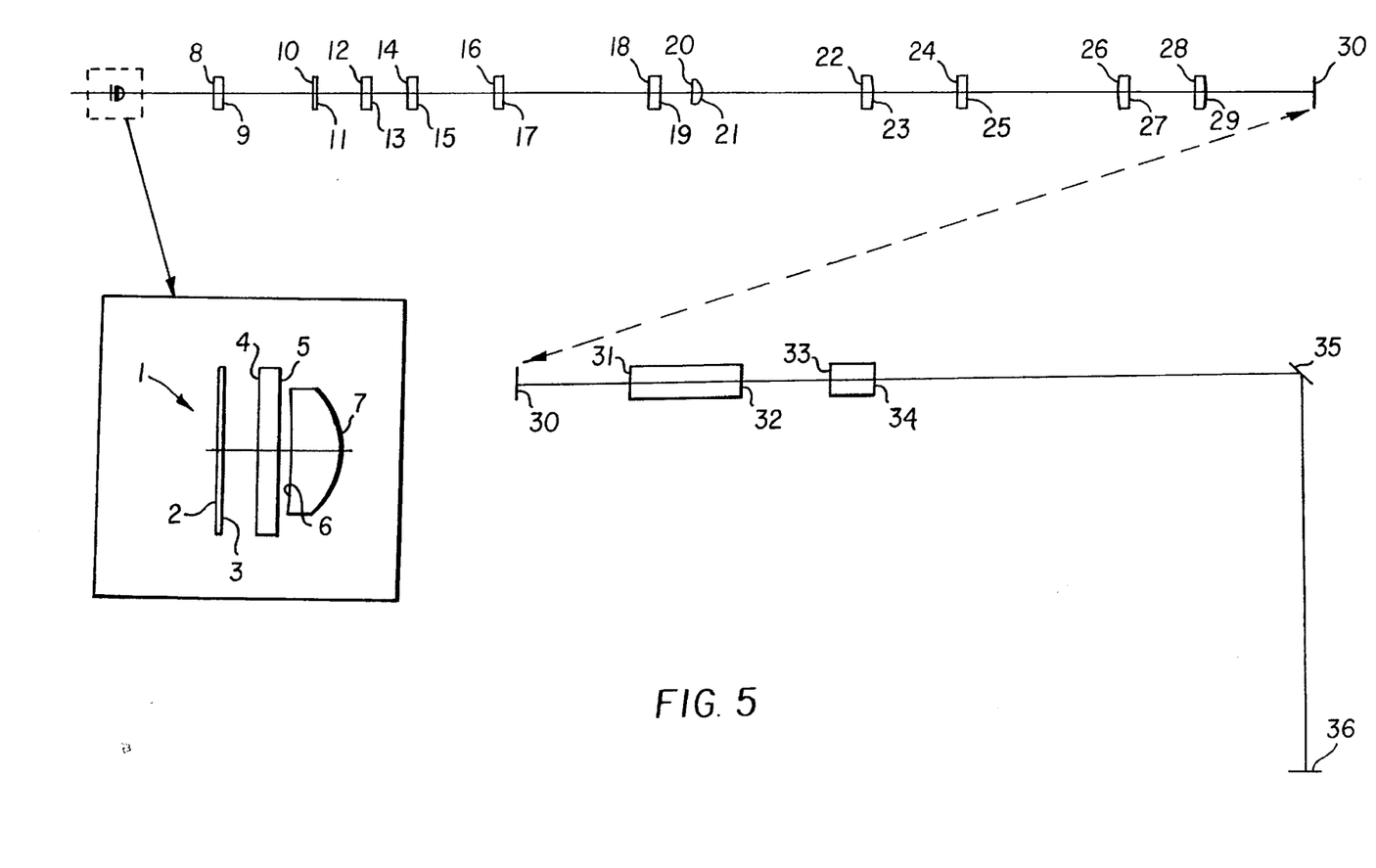
FIG. 5 is a diagrammatic view of the Y section optical system of the anamorphic optical system set out in the Table.
Figure 6:
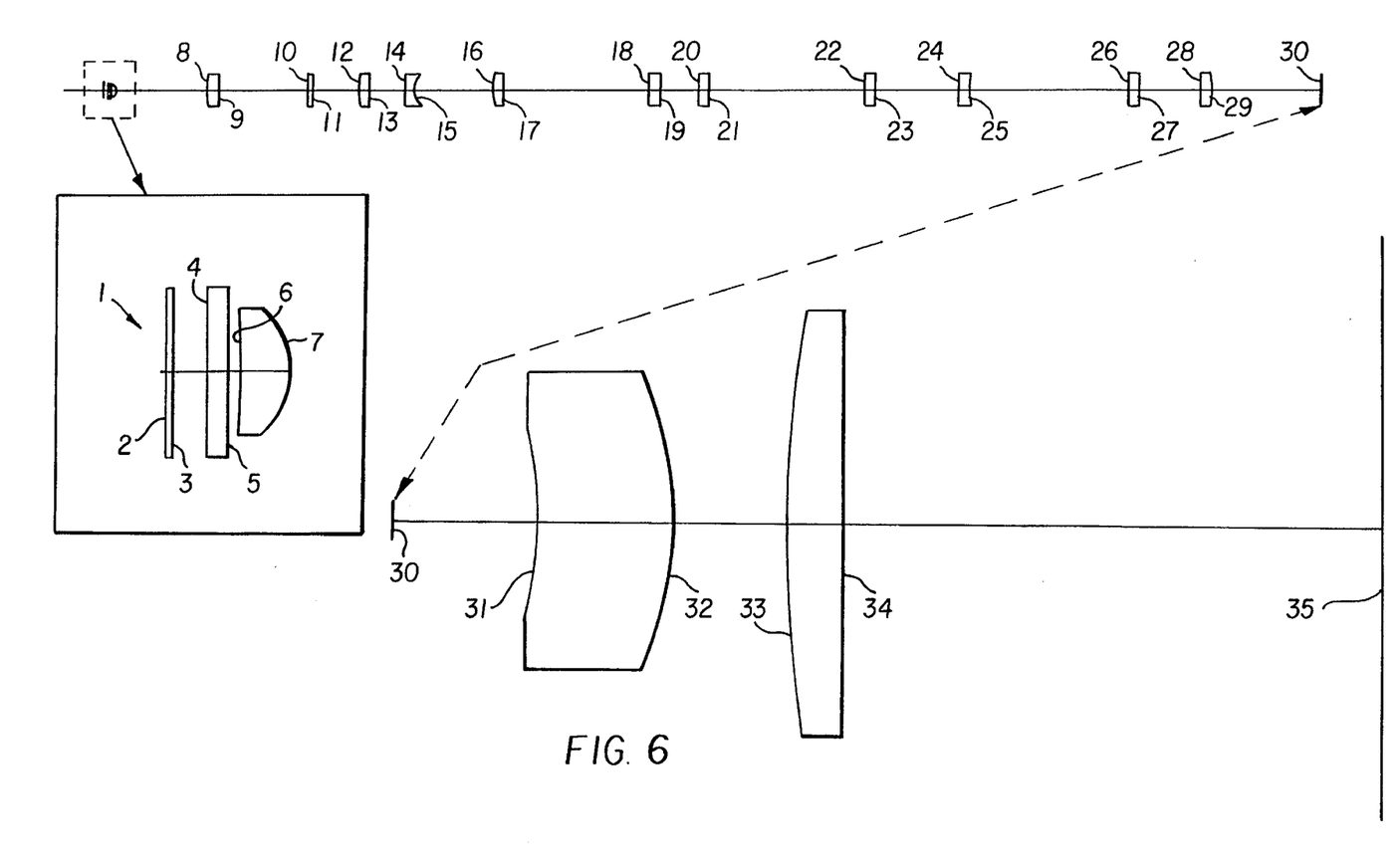
FIG. 6 is a diagrammatic view of the X section optical system of the anamorphic optical system set out in the Table.

A third embodiment shown in FIGS. 5 and 6 and listed in Table I below applies to an orthogonal anamorphic optical system. In this embodiment, only one section of the optical system satisfies the criterion of the invention by having its second principal focus at the image receiving medium.

TABLE I

| Surface | Y Radius | X Radius | Space | Refractive Index |
|---|---|---|---|---|
| 1 | 0 | 0 | 0.2795 | Laser |
| 2 | 0 | 0 | 0.25 | 1.514 |
| 3 | 0 | 0 | 1.605 | |
| 4 | 0 | 0 | 1.029 | 1.514 |
| 5 | 0 | 0 | 0.5 | |
| 6 | −47.7003 | −47.7003 | 2.269 | 1.833 |
| 7 | −3.5786 | −3.5786 | 42.362 | |
| 8 | 0 | 100.381 | 5.08 | 1.514 |
| 9 | 0 | 0 | 41.008 | |
| 10 | 0 | 0 | 1.95 | 1.508 |
| 11 | 0 | 0 | 20.707 | |
| 12 | 66.552 | 66.552 | 5.08 | 1.514 |
| 13 | 0 | 015.904 | | |
| 14 | 0 | 0 | 5.08 | 1.514 |
| 15 | 0 | 11.1633 | 35.861 | |
| 16 | 0 | 19.98 | 5.08 | 1.514 |
| 17 | 0 | 0 | 66.298 | |
| 18 | 0 | 0 | 6 | 2.401 |
| 19 | 0 | 0 | 16.748 | |
| 20 | 0 | 0 | 5.08 | 1.514 |
| 21 | −9.819 | 0 | 70.139 | |
| 22 | 0 | 0 | 5.08 | 1.514 |
| 23 | −66.2686 | 0 | 38.517 | |
| 24 | 0 | 0 | 5.08 | 1.514 |
| 25 | 0 | 32.0404 | 72.071 | |
| 26 | 0 | 0 | 5.08 | 1.514 |
| 27 | −36.1696 | 0 | 26.835 | |
| 28 | 0 | 0 | 5.08 | 1.514 |
| 29 | 074.7421 | 074.7421 | 49.998 | |
| 30 | 0 | 0 | 44.991 | Deflector |
| 31 | −174.548 | −174.548 | 50.905 | 1.614 |
| 32 | −136.547 | −136.547 | 41.155 | |
| 33 | 0 | 514.985 | 20.19 | 1.514 |
| 34 | 182.118 | 0 | 195.944 | |
| 35 | −231.909 | 0 | 184.843 | Reflector |
| 36 | 0 | | | Image |

In the above Table I under the headings "Y Radius" and "X Radius", the number "0" refers to a flat surface without any curvature. The optical axis is Z and with one section of the orthogonal anamorphic system is labeled Y and the other X. This optical system has its Y section second principal focus located on the image receiving medium, surface 36 in the table. The light source which is a solid state laser is located at surface 1, which coincides with the first principal focus of the Y section optical system. The Y section optical system consists of lenses 6-7, 12-13, 20-21, 22-23, 26-27, 28-29, 31-32, 33-34, and mirror 35 as the image forming means. The second principal focus of the Y section optical system coincides with surface 36 which is on the image receiving medium. The light source itself is anamorphic with divergence's of 29 degrees and 8 degrees in the X and Y sections respectively, as measured to the width of the far field intensity at half the peak intensity value. Such a light source is sometimes called an elliptical Gaussian beam because the intensity profile has contours of constant intensity which are substantially elliptical. Such an intensity profile is described by:

$$I(x,y) = I_0 e^{-(x/2\omega_{0x})^2 - (y/2\omega_{0y})^2}$$

In the above equation, z is along the optical axis and x and y are transverse positions from the optical axis. The peak intensity is $I_0$ and $\omega_{0x}$ and $\omega_{0y}$ are the x and y "waist radii" respectively, namely half the diameter at which the intensity falls to $e^{-2}$ of the peak intensity, $I_0$.

Both the X waist and Y waists are located very near the image surface of the above embodiment. In the X section of the optical system in the above embodiment, the second principal focus is not at the image receiving medium.

The table shows cylindrical components such as the lens from surfaces 8 to 9 with 0 radius in the no optical power section and with the radius given for the section with optical power. The component from surfaces 8 to 9 is a cylindrical lens with positive power in the X section on the surface facing the laser diode, and no power in the Y section. The surface facing the image receiving media is flat because both radii are zero.

The system has a magnification of approximately 160 from the laser on surface 1 to the image receiving medium on surface 36. By carefully designing the system so that the image medium is located at the second principal focus, variation of the writing spot size is thus minimized.

Industrial Application and Advantages

The disclosed laser scanner has application in laser printers and laser scanning systems. An advantage of the invention is that it allows practical laser scanners having higher magnification to be used. A further advantage is the elimination or simplification of expensive athermal laser diode assemblies.

Although the invention has been described in detail with particular reference to a preferred embodiment thereof, it will be understood that variations and modifications can be effected within the spirit and scope of the invention as described above and as defined in the appended claims.

What is claimed is:

1. An imaging system comprising:
   means defining an image plane;
   a light source; and
   an optical system located between said light source and said means defining an image plane, said optical system having an optical axis, a first principal focus and a second principal focus,
   wherein said means defining an image plane is located at said second principal focus of said optical system, and wherein said optical system creates a Gaussian intensity profile on said image plane whose $e^{-2}$ intensity diameter on said plane is substantially constant even when said light source being imaged by said optical system is shifted by thermal effects along the optical axis.

2. The imaging system of claim 1 wherein said light source is located at said first principal focus of said optical system.

3. The imaging system of claim 1 wherein said light source is a laser diode.

4. The imaging system of claim 1 wherein an image receiving medium is located at said means defining an image plane.

5. An imaging system comprising:
   means defining an image plane;
   a light source; and
   an anamorphic optical system located between said light source and said means defining an image plane, said anamorphic optical system having at least one principal section of symmetry having an optical axis, a first principal focus and a second principal focus,
   wherein said means defining an image plane is located at said second principal focus of said at least one principal section of said optical system, and wherein said optical system creates a Gaussian intensity profile on said image plane whose $e^{-2}$ intensity diameter on said plane is substantially constant even when said light source being imaged by said optical system is shifted by thermal effects along the optical axis.

6. The imaging system of claim 5 wherein said light source is an elliptical Gaussian.

7. The imaging system of claim 5 wherein said light source is a laser diode.

8. The imaging system of claim 5 wherein an image receiving medium is located at said means defining an image plane.

* * * * *